US005550240A

United States Patent [19]

Mahó et al.

[11] Patent Number: 5,550,240
[45] Date of Patent: Aug. 27, 1996

[54] PIPERAZINYL-BIS (ALKYLAMINO)PYRIMIDINE DERIVATIVES AND PROCESS FOR PREPARING SAME

[75] Inventors: Sándor Mahó; Zoltán Tuba; Csaba Sánta; Gábor Balogh; Éva Czajlikné Csizér; Mária Lovasné Marsai; György Gálik, all of Budapest, Hungary

[73] Assignee: Richter Gedeon Vegyeszeti Gyar Rt., Budapest, Hungary

[21] Appl. No.: 351,449

[22] PCT Filed: Jun. 8, 1993

[86] PCT No.: PCT/HU93/00034

§ 371 Date: Dec. 8, 1994

§ 102(e) Date: Dec. 8, 1994

[87] PCT Pub. No.: WO93/25539

PCT Pub. Date: Dec. 23, 1993

[30] Foreign Application Priority Data

Jun. 9, 1992 [HU] Hungary .................................... 1907/92

[51] Int. Cl.$^6$ ...................... C07D 403/04; A61K 31/505
[52] U.S. Cl. ........................... 544/295; 514/212; 514/252; 540/601
[58] Field of Search ............................ 544/295; 540/601; 514/212, 252

[56] References Cited

U.S. PATENT DOCUMENTS

| | | | |
|---|---|---|---|
| 4,916,133 | 4/1990 | Manoury et al. | 514/252 |
| 4,980,350 | 12/1990 | MacCoss et al. | 514/245 |
| 4,996,318 | 2/1991 | Gall et al. | 544/295 |
| 5,099,019 | 3/1992 | McCall et al. | 544/295 |
| 5,120,843 | 6/1992 | McCall et al. | 544/295 |
| 5,382,661 | 1/1995 | McCall | 544/295 |

FOREIGN PATENT DOCUMENTS

| | | | |
|---|---|---|---|
| 0263213 | 4/1988 | European Pat. Off. | 514/252 |
| 1345640 | 1/1974 | United Kingdom | 514/252 |

*Primary Examiner*—Mukund J. Shah
*Assistant Examiner*—Matthew V. Grumbling
*Attorney, Agent, or Firm*—Herbert Dubno; Jonathan Myers

[57] ABSTRACT

An intermediate compound is disclosed that is useful in the preparation of a lipid-peroxidation inhibiting substance and that is selected from the group consisting of:

2,4-bis[1-adamantylamino]-6-(1-piperazinyl)pyrimidine; and 4,6-bis(1-adamantylamino)-2-(1-piperazinyl)pyrimidine; or a pharmaceutically acceptable acid addition salt thereof.

2 Claims, No Drawings

PIPERAZINYL-BIS (ALKYLAMINO)PYRIMIDINE DERIVATIVES AND PROCESS FOR PREPARING SAME

This is a natural stage application under 37 C.F.R. 371 of PCT/HU93/00034, filed Jun. 8, 1993.

FIELD OF THE INVENTION

The invention relates to novel piperazinyl-bis(alkylamino)pyrimidine derivatives of the formula

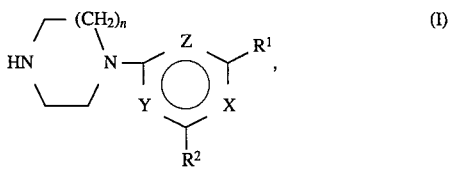

wherein
two of X, Y and Z mean a nitrogen atom each and the third one is a methine group;

$R^1$ and $R^2$ are each, independently from each other, a primary amino group bearing as substituent a branched-chain $C_{4-8}$alkyl, -alkenyl or -alkynyl group, or a $C_{4-10}$cycloalkyl group comprising 1 to 3 ring(s) and being optionally substituted by $C_{1-3}$alkyl group(s); or $R^1$ and $R^2$ are each for a spiro-heterocyclic secondary amino group containing at most 10 carbon atoms and optionally at least one oxygen atom as an additional heteroatom; or one of $R^1$ and $R^2$ is an unsubstituted heterocyclic secondary amino group containing 4 to 7 carbon atoms and the other one is an above-identified primary amino group, an above-identified spiro-heterocyclic secondary amino group, or a heterocyclic secondary amino group containing 4 to 7 carbon atoms and substituted by $C_{1-4}$alkyl group(s); and n is 1 or 2,
as well as their acid addition salts.

Further, the invention relates to a process for the preparation of the above compounds.

The compounds of the formula (I) according to the invention are new and possess a significant biological activity in themselves; however, their use in the preparation of lipid peroxidation-inhibiting substances bears a greater importance.

Hereinafter and in the claims primary amino groups are meant to contain a hydrogen atom as one substituent whereas the other substituent is a branched-chain $C_{4-8}$alkyl, -alkenyl or -alkynyl group, or a $C_{4-10}$cycloalkyl group, comprising 1 to 3 rings, and being optionally substituted by $C_{1-3}$alkyl group(s). The branched-chain $C_{4-8}$alkyl, -alkenyl and -alkynyl groups may be various iso-, sec- and teft-butyl, butenyl, pentyl, pentenyl, pentynyl, hexyl, hexenyl, hexynyl, pentyl, heptenyl, heptynyl, octyl, octenyl and octynyl groups. Preferred representatives of these are the 1,1-dimethylethyl, 2,2-dimethylpropyl and 4,4-dimethyl-1-penten-5-yl groups.

The $C_{4-10}$cycloalkyl group comprising 1 to 3 rings and being optionally substituted by $C_{1-3}$alkyl group(s) can be e.g. a cyclobutyl, cyclopentyl, cyclohexyl, cycloheptyl or adamantyl group. These groups may be unsubstituted or bear one or more methyl, ethyl or propyl group(s) as substituents.

As $R^1$ and $R^2$, the spiro-heterocyclic secondary amino group containing at most 10 carbon atoms and optionally at least one additional oxygen heteroatom is exemplified by the 4,4-ethylenedioxy-1-piperidinyl group, without any limitation thereto.

When representing an unsubstituted heterocyclic secondary amino group containing 4 to 7 carbon atoms, one of $R^1$ and $R^2$ may preferably be a pyrrolidino, piperidino or azepino group. In this case, the other one of $R^1$ and $R^2$ means either a primary amino group mentioned above, or an above-defined secondary heterocyclic group having spiro structure, or an above-defined heterocyclic secondary amino group containing 4 to 7 carbon atoms and substituted by $C_{1-4}$alkyl group(s). These $C_{1-4}$alkyl groups may be the same or different, e.g. methyl, ethyl, n- or isopropyl, or n-, iso-, secor tert-butyl groups. A preferred representative of these substituted heterocyclic secondary amino groups is e.g. the 2,2,6,6-tetramethyl-1-piperidinyl group.

BACKGROUND OF THE INVENTION

Lipid peroxidation occurring as a consequence of injuries is a secondary process. Some cells are immediately destroyed when the tissues are damaged. During the next hours the injury is extended to the surrounding cells. This is induced by free oxygen radicals which attack the lipid layer of the cellular membrane and may eventually lead to cell death by damaging the membrane and releasing hydrogen peroxide. Compounds inhibiting lipid peroxidation can prevent this secondary process occurring as sequels of e.g. paralyses, cephalic or spinal traumas. Compounds possessing such an effect may be utilized e.g. for the treatment of Alzheimer's disease, muscular dystrophy and the like.

The following publications discussing the preparation of piperazinylpyrimidine derivatives are known; the preparation of antiinflammatory 2,4-diamino-6-piperazinylpyrimidine derivatives is described in the GB patent specification No. 1,345,640. In the target compounds the amino groups, being the same or different, may be monoalkylamino groups containing 1 to 6 carbon atoms, cycloalkylamino groups containing at most 6 carbon atoms or a morpholino group whereas the amino group in position 4 may be a piperazino group, too.

According to this patent specification the starting substance of the synthesis is 2,4,6-trichloropyrimidine of the formula (IV) (see hereinafter) which is first reacted with morpholine, then the dichloro compound obtained is brought into reaction with ethylamine, finally the monochloro compound formed is reacted with piperazine to give 4-ethylamino-2-morpholino-6-(1-piperazinyl)pyrimidine as described in the examples. Compounds containing a morpholino group as one of the two amino groups and a cycloalkylamino or monoalkylamino group containing at most 4 carbon atoms are indicated to be most effective. Among these in the preferred compounds one of the two amino groups is ethylamino or cyclopropylamino group, the other one is a morpholino group. Detailed examples with physical characteristics are given for the preparation of 2-ethylamino-4-morpholino-6-(1-piperazinyl)pyrimidine and 4-cyclopropylamino-2-morpholino-6-(1-piperazinyl)pyrimidine, too.

In the published German patent specification No. 2,630, 140 2,4-diaminopyrimidine derivatives are described, wherein the amino groups are mono- or disubstituted; the substituents may be $C_{1-4}$alkyl, $C_{2-4}$alkenyl or cyclopropyl groups. A post-emergent herbicidal activity is attributed to these compounds.

The synthesis of [piperazinyl-bis(amino)pyrimidinyl]-steroids of primarily lipid peroxidation-inhibiting activity is described in the published PCT patent application No. WO 87/01706. There are given examples for the preparation of piperazinyl-bis(alkylamino)pyrimidine derivatives used as starting substances for the steroid derivatives mentioned above, too. Thus, 2,4,6-trichloropyrimidine is reacted primarily with saturated or unsaturated amines containing 1 to 3 carbon atoms as well as pyrrolidine, morpholine, hexamethyleneimine or N-methylpiperazine. According to the biological data published in this application, 4-(1-piperazinyl)-2,6-bis(pyrrolidino)pyrimidine proved to be the most favourable one for the preparation of lipid peroxidation-inhibiting compounds.

It is known from the published PCT patent application No. WO P 91/11453 that the strength of the lipid peroxidation-inhibiting effect is significantly influenced by using some-piperazinyl-bis(alkylamino)pyrimidine derivatives as substituents connected e.g. to compounds having steroid skeleton or other substances having a similar structure.

OBJECT OF THE INVENTION

The object of the present invention is aimed at the preparation of analogous piperazinylpyrimidine derivatives which, when used as substituents, are capable of increasing the biological activity and decreasing the toxicity of the molecules substituted by these substituents, in comparison to known analogues.

SUMMARY OF THE INVENTION

Surprisingly, it has been found that the compounds of the formula (I) according to the invention are excellent for this purpose.

The piperazinylpyrimidine compounds according to the invention can be used as substituents for various compounds, e.g. pregnane derivatives.

The novel piperazinyl-bis(alkylamino)pyrimidine derivatives of the formula (I) can be prepared in such a way that a) about 1 mole of a 2,4,6-trichloropyrimidine characterized by formula

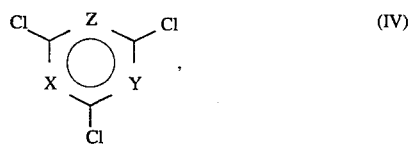

(IV)

wherein X, Y and Z are as defined above, is reacted with about 1 mole of a primary or secondary amine of the formula $R^1$-H, wherein $R^1$ is as defined above, the obtained isomeric mixture of a 2-amino-4,6-dichloropyrimidine of the formula

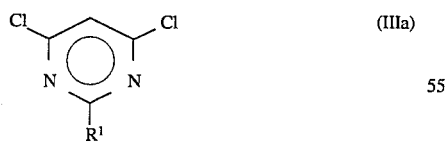

(IIIa)

and a 4-amino-2,6-dichloropyrimidine of the formula

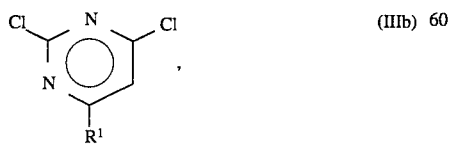

(IIIb)

wherein $R^1$ is as defined above, is separated to the individual isomers, and about 1 mole of a thus obtained individual isomer is reacted with about 1 mole of a primary or secondary amine of the formula $R^2$-H, wherein $R^2$ is as defined above, then after separating the isomeric mixture of diaminochloropyrimidines of the formula

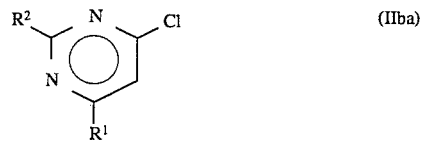

(IIba)

and formula

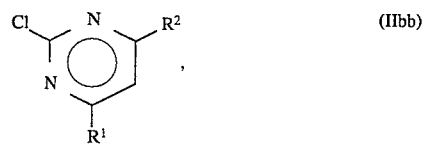

(IIbb)

wherein $R^1$ and $R^2$ are as defined above, obtained from a 4-amino-2,6-dichloropyrimidine of the formula (IIIb), wherein $R^1$ is as defined above, to the individual isomers, one of these individual isomers or a 2,6-diamino-4-chloropyrimidine of the formula

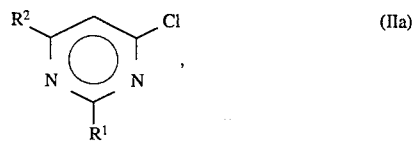

(IIa)

wherein $R^1$ and $R^2$ are as defined above, obtained from a 2-amino-4,6-dichloropyrimidine of the formula (IIIa), is reacted with a piperazine derivative of the formula

(V)

wherein n is 1 or 2; or b) about 1 mole of a 2,4,6-trichloropyrimidine characterized by the formula (IV), wherein X, Y and Z are as defined above, is reacted with about 2 moles of a primary or secondary amine of the formula $R^1$-H, wherein $R^1$ is as defined above, then after separating the obtained isomeric mixture of diaminochloropyrimidines of the formulae (IIba) (IIbb), wherein $R^1$ and $R^2$ are the same as $R^1$ defined above, to the individual isomers, one of these individual isomers is reacted with a piperazine derivative of the formula (V), wherein n is 1 or 2, in order to obtain piperazinyl-bis(alkylamino)pyrimidine derivatives of the formula (I) bearing identical substituents as $R^1$ and $R^2$, wherein X, Y, Z, $R^1$, $R^2$ and n are as defined above, and, if desired, a piperazinyl-bis(alkylamino)pyrimidine derivative of the formula (I) obtained, wherein X, Y, Z, $R^1$, $R^2$ and n are as defined above, is converted into an acid addition salt by reacting it with an acid and/or a free base of the formula (I) is liberated from its acid addition salt.

2,4,6-Trichloropyrimidine used as starting substance in the process of the invention is a well-known compound [Ber. 33, pages 3666 (1900) and 37, page 3657 (1904); Chem. Abstr. Registration No. 3764-01-0]. The primary and secondary amines of the formulae $R^1$-H and $R^2$-H, as well as the piperazine derivatives of the formula (V) are commercially available products.

Depending on the reactivity of the amine, the reaction of a 2,4,6-trichloropyrimidine of the formula (IV) with primary or secondary amines of the formula $R^1$-H may be carried out at a temperature between −20° C. and +40° C. with a reaction time of from 30 minutes up to several days. When using the sterically hindered 2,2,6,6-tetramethylpiperidine (which may be used as a solvent, too) a boiling under reflux for about 50 hours is necessary at the boiling point of the reaction mixture for completing the reaction. The working-up of the reaction mixture as well as the recovery of the product are preferably carried out in such a manner that after termination of the reaction the solvent is distilled off, the residue is dissolved in a halogenated solvent, preferably chloroform, then the solution is washed first with aqueous sodium hydroxide solution and subsequently with water. After separation the organic phase is dried, the solvent is distilled off, then the two alkylamino-dichloropyrimidine isomers formed in the reaction are separated by chromatography on a silica gel column. The separated individual isomers are purified by recrystallization.

After separation the isomeric alkylamino-dichloropyrimidine derivatives of the formula (IIIa) and (IIIb) obtained in the first step are again reacted with the same or different amine. The parameters of this reaction are mainly dependent on the reactivity of the amine reactant. Thus, the reaction can be made complete at room temperature when pyrrolidine is used as an amine; whereas a reaction lasting for about 15 hours at 130° C. is needed in the case of tert-butylamine. The reaction of neopentylamine with the isomeric alkylamino-dichloropyrimidine derivatives can be carried out under milder conditions: this reaction becomes complete by boiling in isopropanol for about 20 hours. The less reactive 5-amino-4,4-dimethyl-1-pentene reacts with the isomeric alkylamino-dichloropyrimidine derivatives only at higher temperatures. Due to its large space demand, 1-aminoadamantane should be reacted, by boiling in n-butanol for about 75 hours.

The recovery of the individual isomers from reaction mixtures containing the diaminochloropyrimidine isomers of the formulae (IIba) and (IIbb), formed from 4-amino-2,6-dichloropyrimidine of the formula (IIIb) in the second step, can be achieved by using e.g. the method described above for the recovery of compounds of the formulae (IIIa) and (IIIb).

According to the invention the preparation of piperazinylpyrimidine derivatives of the formula (I) by reacting bis(alkylamino)-chloropyrimidine derivatives of formulae (IIa), (IIbb) or (IIba) with piperazine derivatives of formula (V) is suitably carried out as described hereinafter.

The bis(alkylamino)-chloropyrimidine derivative of the formula (IIa) or (IIbb) or (IIba) is dissolved in a tertiary amine, preferably N-ethylmorpholine, and boiled with an excess of the piperazine derivative of the formula (V) under nitrogen for about 25 hours. After the reaction has become complete, N-ethylmorpholine used as solvent and the major part of the excess of the piperazine derivative of the formula (V) are distilled off, water is added to the residue and distilled off again. This repeated distillation is continued under atmospheric pressure until the head temperature reaches about 100° C. After dissolving the residue in chloroform the solution is washed first with aqueous sodium hydroxide solution, then with water. After separation the organic phase is dried and the chloroform is distilled off. The residue is purified first by chromatography on a silica gel column and then by recrystallization.

The advantage of using the piperazinyl-bis(alkylamino)pyrimidine derivatives of the formula (I) for the preparation of lipid peroxidation-inhibiting compounds is demonstrated on 21-{4-[2,4-bis(adamantylamino)-6-pyrimidinyl]-1-piperazinyl}-16α-methylpregna-1,4,9(11)triene-3,20-dione methanesulfonate.

The pharmacological study was carried out on unanesthetized mice by using a known experimental cephalic trauma model [J. Neurosurg. 62, page 882 (1980)] modified by us. In this study, the potential cerebroprotective effects of intravenous (i.v.) doses of the compounds were investigated.

A metal cleaver of defined weight was let fall onto a defined part of the scullcap surface of the experimental animals from a defined height under the force of gravity. Within 5 minutes following the closed cephalic injury induced by the cleaver, a suitable dose of the substance under test was injected to a tail vein of the animals and the neurological condition of the animals was evaluated in the 60th minute following the cephalic trauma. This evaluation was performed using a simple grip test, to examine the effects of the trauma on the motor functions of both the upper and lower limbs. In addition, the frequency of cases considered to be "mild" or "severe", based on predetermined criteria, as well as the ratio of animals suffering from paraparesis-paraplegia were registered in the various treatment groups. The development of eventually occurring deficiency symptoms of the nervous system was made quantitative by comparison of the neurological condition of animals treated with the active agent to the condition of controls treated only with the vehicle.

When administered in the most favorable dose of 0.1 mg/kg, 21-{4-[2,4-bis(adamantylamino)-6-pyrimidinyl]-1-piperazinyl}-16α-methylpregna-1,4,9(11)triene-3,20-dione methanesulfonate increased by 33% the number of cases signed as "mild" (based on the neurological symptoms induced by the cephalic trauma) and similarly, it decreased by 33% the frequency of cases involving paraparesis-paraplegia. The known tirilazad mesylate (see the published PCT patent application No. WO 87/01706), chemically 16α-methyl-21-{4-[2,4-bis(pyrrolidino)-6-pyrimidinyl]-1-piperazinyl}Pregna-1,4,9(11)triene-3,20-dione methanesulfonate, was used as control. When administered in the most effective dose of 0.3 mg/kg, tirilazad mesylate increased only by 23% the number of animals showing "mild" deficiency symptoms and decreased only by 20% the frequency of paraplegic animals.

Thus, it is obvious from the experimental results that the compounds according to our invention increase the lipid peroxidation-inhibiting effect of the basic substance to a higher grade in comparison to known compounds having a similar structure.

The invention is illustrated in detail by the aid of the following non-limiting Examples.

EXAMPLE 1

Preparation of 4,6-dichloro-2-pyrrolidinopyrimidine and 2,4-dichloro-6-pyrrolidinopyrimidine After dropping 23.7 ml (286.6 mmoles) of pyrrolidine to a mixture containing 25.0 g (136.3 mmoles) of 2,4,6-trichloropyrimidine in 200 ml of tetrahydrofuran at −20° C. within about 30 minutes, the cooling is stopped and after stirring for an additional 30 minutes the reaction mixture is evaporated. After distributing the residue between 500 ml of chloroform and 50 ml of 10% sodium hydroxide solution, the organic phase is separated, washed 4 times with 150 ml of water each, then dried and evaporated. The residue is subjected to chromatography on a silica gel column. By using a 19:1 hexane/ethyl acetate mixture as eluent the eluate is evaporated and the evaporation residue is recrystallized from hexane to give 7.51 g (25.27%) of 4,6-dichloro-2-pyrrolidinopyrimidine, m.p. 95°–98° C.

$^1$H-NMR (60 MHz, CDCl$_3$) δ ppm: 6.51 (s, 1H, 5-H).

By further elution with a 4:1 mixture of the above solvent system 2,4-dichloro-6-pyrrolidinopyrimidine as the more polar product is obtained in a yield of 20.22 g (68.03%) after recrystallization from hexane, m.p.: 100.5°–103.5° C.
$^1$H-NMR (60 MHz, CDCl$_3$) δ ppm: 6.18 (s, 1H, 5-H).

EXAMPLE 2

Preparation of 4,6-dichloro-2-(1,1-dimethylethylamino)pyrimidine and 2,6-dichloro-4-(1,1-dimethylethylamino)pyrimidine 25 g (136.6 mmoles) of 2,4,6-trichloropyrimidine are dropwise added to a mixture of 31.52 ml of 1-amino-1,1-dimethylethane and 200 ml of tetrahydrofuran at a temperature between 10° C. and 15° C. while cooling and stirring. The reaction mixture is stirred at room temperature for an additional 5 hours, then evaporated. After distributing the residue between 50 ml of chloroform and 50 ml of 10% sodium hydroxide solution and separating, the organic phase is washed 4 times with 150 ml of water each, then dried and evaporated. The residue is separated by chromatography on a silica gel column by using mixtures of hexane and ethyl acetate as eluent. By using 9:1 hexane/ethyl acetate mixture 4,6-dichloro-2-(1,1-dimethylethylamino)pyrimidine is eluated which is recrystallized from hexane to obtain a yield of 11.35 g (37.84%), m.p.: 70°–74° C.

$^1$H-NMR (60 MHz, THF-d$_8$) δ ppm: 6.63 (s, 1H, 5-H).

By continuing the elution with a 4:1 mixture of the above solvent system 2,6-dichloro-4-(1,1-dimethylethylamino)pyrimidine as a more polar product is obtained, which is recrystallized from ethyl acetate to give 13.31 g (44.35%) of pure product, m.p.:192°–195° C.

$^1$H-NMR (60 MHz, THF-d$_8$) δ ppm: 6.32 (s, 1H, 5-H).

EXAMPLE 3

Preparation of 4-chloro-2,6-bis(1,1-dimethylethylamino)pyrimidine

A solution containing 5.0 g of 4,6-dichloro-2-(1,1-dimethylethylamino)pyrimidine in 25 ml of 1-amino-1,1-dimethylethane is heated in a closed tube at 130° C. for 15 hours. Thereafter, the reaction mixture is evaporated and the evaporation residue is distributed between 80 ml of chloroform and 15 ml of 10% sodium hydroxide solution. After separation the organic phase is washed 4 times with 20 ml of water each, then dried and evaporated. The evaporation residue is recrystallized from hexane to give the title compound in a yield of 5.45 g (93.4%), m.p.: 128°–130° C.

$^1$H-NMR (60 MHz, THF-d$_8$) δ ppm: 5.67 (s, 1H, 5-H).

EXAMPLE 4

Preparation of 2,4-bis(1,1-dimethylethylamino)-6-(1-piperazinyl)pyrimidine

A mixture containing 9.58 g (34.7 mmoles) of 4-chloro-2,6-bis(1,1-dimethylethylamino)pyrimidine, 11.95 g (138.8 mmoles) of piperazine and 150 ml of N-ethylmorpholine is boiled under reflux and nitrogen atmosphere for 25 hours, then the solvent and the excess of piperazine are distilled off under atmospheric pressure. Subsequently, 100 ml of water are added to the residue and the distillation is continued until the head temperature reaches 100° C. After cooling down, the residue is distributed between 200 ml of chloroform and 30 ml of 10% sodium hydroxide solution. After separation the organic phase is washed 4 times with 50 ml of water each, then dried and evaporated. The residue is purified by chromatography on a silica gel column by using a 9:1 mixture of chloroform/methanol as eluent. After evaporating the eluate the residue is recrystallized from hexane to obtain the title compound in a yield of 64%, m.p.: 142°–145° C.

$^1$H-NMR (60 MHz, CDCl$_3$) δ ppm: 4.99 (s, 1H, 5-H).

EXAMPLE 5

Preparation of 6-chloro-2,4-bis (1,1-dimethylethylamino)pyrimidine and 2-chloro-4,6-bis (1,1-dimethylethylamino) pyrimidine A solution of 10 g of 2,6-dichloro-4-(1,1-dimethylethylamino)pyrimidine in 50 ml of 1-amino-1,1-dimethylethane is heated in a closed tube at 130° C. for 15 hours. Thereafter, the reaction mixture is evaporated and the residue is distributed between 150 ml of chloroform and 30 ml of 10% sodium hydroxide solution. After separation the organic phase is washed 4 times with 10 ml of water each, then dried and evaporated. The evaporation residue is subjected to chromatography on a silica gel column by using a 9:1 mixture of hexane/ethyl acetate as eluent to give 6-chloro-2,4-bis(1,1-dimethylethylamino) pyrimidine which is recrystallized from hexane to result in a yield of 9.92 g (85.1%), m.p.: 125°–127° C. By continuing the elution with a 4:1 mixture of hexane/ethyl acetate 2-chloro-4,6-bis(1,1-dimethylethylamino)pyrimidine as a more polar product is obtained which is recrystallized from hexane to result in a yield of 0.49 g (4.2%), m.p.: 132°–135° C.

$^1$H-NMR (60 MHz, CDCl$_3$) δ ppm: 4.93 (s, 1H, 5-H).

EXAMPLE 6

Preparation of 4,6-bis(1,1-dimethylethylamino)-2-(1-piperazinyl)pyrimidine

By reacting 2-chloro-4,6-bis(1,1-dimethylethylamino)-pyrimidine with piperazine as described in Example 4, the title product is obtained in a yield of 76.5%, m.p.: 135°–138° C.

$^1$H-NMR (60 MHz, CDCl$_3$) δ ppm: 4.83 (s, 1H, 5-H).

EXAMPLE 7

Preparation of 1-[2,4-bis(1,1-dimethylethylamino)-6-pyrimidinyl]-hexahydro-1H-1,4-diazepine By reacting 4-chloro-2,6-bis(1,1-dimethylethylamino)-pyrimidine with hexahydro-1H-1,4-diazepine as described in Example 4, the title product is obtained in a yield of 55.3%, m.p.: 127°–132° C.

$^1$H-NMR (60 MHz, CDCl$_3$) δ ppm: 4.96 (s, 1H, 5-H).

EXAMPLE 8

Preparation of 6-chloro-2-(1,1-dimethylethylamino)-4-(2,2-dimethylpropylamino)pyrimidine After dissolving 5.0 g of 4,6-dichloro-2-(1,1-dimethylethylamino)pyrimidine in 25 ml of isopropanol and adding 5 ml of 1-amino-2,2-dimethylpropane the reaction mixture is boiled under reflux for 20 hours. Then, the reaction mixture is evaporated and the residue is distributed between 80 ml of chloroform and 15 ml of 10% sodium hydroxide solution. After separation the organic phase is washed 4 times with 20 ml of water each, then dried and evaporated. After recrystallizing the evaporation residue from hexane the title product is obtained in a yield of 4.49 g (73%), m.p.: 109.5°–111° C.

$^1$H-NMR (60 MHz, CDCl$_3$) δ ppm: 5.71 (s, 1H, 5-H).

EXAMPLE 9

Preparation of 2-(1,1-dimethylethylamino)-4-(2,2-dimethylpropylamino)-6-(1-piperazinyl)pyrimidine By reacting 6-chloro-2-(1,1-dimethylethylamino)-4-(2,2-dimethylpropylamino)pyrimidine with piperazine as described in Example 4, the title product is obtained in a yield of 86.0%, m.p.: 120°–124° C.

$^1$H-NMR (60 MHz, CDCl$_3$) δ ppm: 4.96 (s, 1H, 5-H).

EXAMPLE 10

Preparation of 6-chloro-4-(1,1-dimethylethylamino)-2-(2,2-dimethylpropylamino)pyrimidine After dissolving 5.0 g of 2,4-dichloro-6-(1,1-dimethylethylamino)pyrimidine in 25 ml of isopropanol and adding 5 ml of 1-amino-2,2-dimethylpropane, the reaction mixture is boiled under reflux for 20 hours. Subsequently, the reaction mixture is evaporated and the residue is distributed between 80 ml of chloroform and 15 ml of 10% sodium hydroxide solution. After separation the organic phase is washed 4 times with 20 ml of water each, then dried and evaporated. The evaporation residue is purified by chromatography on a silica gel column by using a 9:1 mixture of hexane/ethyl acetate as eluent. After recrystallizing the eluted product from hexane, the title product is obtained in a yield of 4.05 g (65.9%), m.p.: 115°–119° C.

$^1$H-NMR (60 MHz, CDCl$_3$) δ ppm: 5.66 (s, 1H, 5-H).

EXAMPLE 11

Preparation of 4-(1,1-dimethylethylamino)-2-(2,2-dimethylpropylamino)-6-(1-piperazinyl)pyrimidine The reaction of 4-chloro-6-(1,1-dimethylethylamino)-2-(2,2-dimethylpropylamino)pyrimidine with piperazine as described in Example 4 gives the title product in a yield of 82.3%, m.p.: 146°–148° C.

$^1$H-NMR (60 MHz, CDCl$_3$) δ ppm: 5.02 (s, 1H, 5-H).

EXAMPLE 12

Preparation of 4-chloro-2-(1,1-dimethylethylamin)-6-pyrrolidinopyrimidine

After adding 10 g of 4,6-dichloro-2-(1,1-dimethylethylamino)pyrimidine in small portions to 40 ml of pyrrolidine at a temperature below 10° C. while cooling and stirring, the reaction mixture is stirred at room temperature for 1 hour and then evaporated. The residue is distributed between 150 ml of chloroform and 30 ml of 10% sodium hydroxide solution. After separation the organic phase is washed 4 times with 50 ml of water each, then dried and evaporated. After recrystallizing the evaporation residue from ethyl acetate the title product is obtained in a yield of 10.76 g (93%), m.p.:153°–157° C.

$^1$H-NMR (60 MHz, CDCl$_3$) δ ppm: 5.67 (s, 1H, 5-H).

EXAMPLE 13

Preparation of 2-(1,1-dimethylethylamino)-4-(1-piperazinyl)-6-pyrrolidinopyrimidine The reaction of 4-chloro-2-(1,1-dimethylethylamino)-6-pyrrolidinopyrimidine with piperazine as described in Example 4 gives the title product in a yield of 78.1%, m.p.: 162°–165° C.

$^1$H-NMR (60 MHz, CDCl$_3$) δ ppm: 4.87 (s, 1H, 5-H).

EXAMPLE 14

Preparation of 4-chloro-6-(1,1-dimethylethylamino)-2-pyrrolidinopyrimidine

By reacting 2,4-dichloro-6-(1,1-dimethylethylamino)pyrimidine with pyrrolidine as described in Example 12, the title product is obtained in a yield of 73.8%, m.p.: 148°–150° C.

$^1$H-NMR (60 MHz, CDCl$_3$) δ ppm: 5.62 (s, 1H, 5-H).

EXAMPLE 15

Preparation of 4-(1,1-dimethylethylamino)-6-(1-piperazinyl)-2-pyrrolidinopyrimidine 4-Chloro-6-(1,1-dimethylethylamino)-2-pyrrolidinopyrimidine is reacted with piperazine as described in Example 4 to give the title product in a yield of 67.5%, m.p.: 140°–145° C.

$^1$H-NMR (60 MHz, CDCl$_3$) δ ppm: 4,90 (s, 1H, 5-H).

EXAMPLE 16

Preparation of 4,6-dichloro-2-(2,2-dimethylpropylamino)pyrimidine and 2,6-dichloro-4-(2,2-dimethylpropylamino)pyrimidine After dropwise adding 25 g (136.3 mmoles) of 2,4,6-trichloropyrimidine to the solution of 23.84 g (273.5 mmoles) of 1-amino-2,2-dimethylpropane in 200 ml of tetraydrofuran at a temperature between 10° C. and 15° C. under cooling and stirring, the reaction mixture is stirred at room temperature for an additional 30 minutes, then evaporated. The evaporation residue is distributed between 300 ml of chloroform and 50 ml of 10% sodium hydroxide solution. After separation the organic phase is washed 4 times with 100 ml of water each, then dried and evaporated. The evaporation residue is subjected to chromatography on a silica gel column by using mixtures of hexane and ethyl acetate as eluent. By elution with a 19:1 mixture of hexane/ethyl acetate 4,6 -dichloro-2-(2,2-dimethylpropylamino) pyrimidine is obtained which is recrystallized from a mixture of ether and hexane to give a yield of 13.60 g (42.6%), m.p.: 63°–66° C.

$^1$H-NMR (60 MHz, CDCl$_3$) δ ppm: 6.60 (s, 1H, 5-H).

By further elution with a 6:1 mixture of hexane/ethyl acetate 2,6-dichloro-4-(2,2-dimethylpropylamino) pyrimidine is obtained, which is recrystallized from a mixture of ether and hexane to result in a yield of 14.24 g (44.6%), m.p.:77°–79° C.

$^1$H-NMR (60 MHz, CDCl$_3$) δ ppm: 6.33 (s, 1H, 5-H).

EXAMPLE 17

Preparation of 4-chloro-2,6-bis(2,2-dimethylpropylamino)pyrimidine

The reaction of 4,6-dichloro-2-(2,2-dimethylpropylamino)pyrimidine with 1-amino-2,2-dimethylpropane as described in Example 10 affords the title product in a yield of 49.4%, m.p.: 95°–98° C.

$^1$H-NMR (60 MHz, CDCl$_3$) δ ppm: 5.71 (s, 1H, 5-H).

EXAMPLE 18

Preparation of 2,4-bis(2,2-dimethylpropylamino)-6-(1-piperazinyl)pyrimidine

The reaction of 4-chloro-2,6-bis(2,2-dimethylpropylamino)pyrimidine with piperazine as described in Example 4 gives the title product in a yield of 51.5%, m.p.: 138°–140° C.

$^1$H-NMR (60 MHz, CDCl$_3$) δ ppm: 4.98 (s, 1H, 5-H).

EXAMPLE 19

Preparation of 6-chloro-2,4-bis(2,2-dimethylpropylamino)pyrimidine and 2-chlore-4,6-bis(2,2-dimethylpropylamino) pyrimidine After dissolving 5.0 g of 2,4-dichloro-6-(2,2-dimethylpropylamino)pyrimidine in 25 ml of isopropanol and adding 5 ml of 1-amino-2,2-dimethylpropane, the reaction mixture is boiled under reflux for 20 hours, then evaporated. The evaporation residue is distributed between 80 ml of chloroform and 15 ml of 10% sodium hydroxide solution. After separation the organic phase is washed 4 times with 20 ml of water each, then dried and evaporated. The residue is purified by chromatography on a silica gel column by using mixtures of hexane and ethyl acetate as eluent. By eluting with a 99:1 mixture 4-chloro-2,6-bis(2,2-dimethylpropylamino)pyrimidine is obtained, which is recrystallized from hexane to result in a yield of 5.00 g (82.3%), m.p.: 95°–97° C.

By further elution with a 19:1 mixture of the above solvent system 2-chloro-4,6-bis(2,2-dimethylpropylamino)pyrimidine as a more polar product is obtained, which is recrystallized from hexane to give a yield of 0.30 g (4.9%), m.p.: 178°–185° C.

EXAMPLE 20

Preparation of 4,6-bis(2,2-dimethylpropylamino)-2-(1-piperazinyl)pyrimidine

The reaction of 2-chloro-4,6-bis(2,2-dimethylpropylamino)pyrimidine with piperazine as described in Example 4 leads to the title product in a yield of 78.3%, m.p.: 132°–136° C.

$^1$H-NMR (60 MHz, CDCl$_3$) δ ppm: 4.85 (s, 1H, 5-H).

EXAMPLE 21

Preparation of 4-chloro-2-(2,2-dimethylpropylamino)-6-pyrrolidinopyrimidine

The reaction of 4,6-dichloro-2-(2,2-dimethylpropylamino)pyrimidine with pyrrolidine as described in Example 12 gives the title product in a yield of 96.7%, m.p.: 147°–150° C.

$^1$H-NMR (60 MHz, CDCl$_3$) δ ppm: 5.67 (s, 1H, 5-H).

EXAMPLE 22

Preparation of 2-(2,2-dimethylpropylamino)-4-(1-piperazinyl- 6-pyrrolidinopyrimidine By reacting 2-(2,2-dimethylpropylamino)-4-chloro-6-pyrrolidinopyrimidine with piperazine as described in Example 4, the title compound is obtained in a yield of 76%, m.p.: 118°–120 °C.

$^1$H-NMR (60 MHz, CDCl$_3$) δ ppm: 4.83 (s, 1H, 5-H).

EXAMPLE 23

Preparation of 4-chloro-6-(2,2-dimethylpropylamino)-2-pyrrolidinopyrimidine

The reaction of 2,4-dichloro-6-(2,2-dimethylpropylamino)pyrimidine with pyrrolidine as described in Example 12 affords the title compound in a yield of 75.0%, m.p.: 130°–135° C.

$^1$H-NMR (60 MHz, CDCl$_3$) δ ppm: 5.72 (s, 1H, 5-H).

EXAMPLE 24

Preparation of 4-(2,2-dimethylpropylamino)-6-(1-piperazinyl)- 2-pyrrolidinopyrimidine The reaction of 4-chloro-6-(2,2-dimethylpropylamino)-2-pyrrolidinopyrimidine with piperazine as described in Example 4 gives the title compound in a yield of 76.0%, m.p.: 140°–145° C.

$^1$H-NMR (60 MHz, CDCl$_3$) δ ppm: 4.93 (s, 1H, 5-H).

EXAMPLE 25

Preparation of 4,6-dichloro-2-[(2,2-dimethyl-4-penten-1yl)-amino]pyrimidine and 2,6-dichloro-4-[(2,2-dimethyl-4-penten-1-yl)amino]pyrimidine 4.59 (25 mmoles) of 2,4,6-trichloropyrimidine are added to a solution of 6.23 g (55 mmoles) of 5-amino-4,4-dimethyl-1-pentene in 50 ml of tetrahydrofuran at room temperature, the reaction mixture is stirred at the same temperature for 4 hours, then evaporated. The evaporation residue is distributed between 60 ml of chloroform and 5 ml of 10% sodium hydroxide solution. After separation the organic phase is washed 4 times with 10 ml of water each, then dried and evaporated. The evaporation residue is subjected to chromatography on a silica gel column by using mixtures of hexane and ethyl acetate as eluents. Elution with a 19:1 hexane/ethyl acetate mixture gives 4,6-dichloro-2-[(2,2-dimethyl-4-penten-1-yl)amino]pyrimidine as an oily product in a yield of 2.62 g (40.3%).

$^1$H-NMR (60 MHz, CDCl$_3$) δ ppm: 6.61 (s, 1H, 5-H).

By continuing the elution with a 9:1 mixture of hexane/ethyl acetate 2,6-dichloro-4-[(2,2-dimethyl-4-penten-1-yl)amino]pyrimidine as a molar polar product is obtained as an oil in a yield of 2.99 g (45.9%).

$^1$H-NMR (60 MHz, CDCl$_3$) δ ppm: 6.34 (s, 1H, 5-H).

EXAMPLE 26

Preparation of 4-chloro-2,6-[(2,2-dimethyl-4-penten-1-yl)amino]pyrimidine

After adding 2,29 (20.2 mmoles) of 5-amino-4,4 -dimethyl-1-pentene to a solution containing 2.5 g (9.61 mmoles) of 4,6-dichloro-2-[(2,2-dimethyl-4-penten-1-yl) amino]pyrimidine in 25 ml of n-butanol, the reaction mixture is boiled under reflux for 10 hours, then evaporated. The evaporation residue is distributed between 50 ml of chloroform and 5 ml of 10% sodium hydroxide solution. After separation the organic phase is washed 4 times with 10 ml of water each, then dried and evaporated. The evaporation residue is purified by chromatography on a silica gel column. By using a 19:1 mixture of hexane/ethyl acetate the title compound is obtained as an oily product in a yield of 2.25 g (69.5%).

$^1$H-NMR (60 MHz, CDCl$_3$) δ ppm: 5.70 (s, 1H, 5-H).

EXAMPLE 27

Preparation of 2,4-bis[(2,2-dimethyl-4-penten-1-yl)amino] -6 -(1-piperazinyl)pyrimidine The reaction of 4-chloro-2,6-bis[(2,2-dimethyl-4-penten-5-yl) amino]pyrimidine with piperazine as described in Example 4 gives the title compound in a yield of 73.2%, m.p.: 72°–84° C.

$^1$H-NMR (60 MHz, CDCl$_3$) δ ppm: 4.83 (s, 1H, 5-H).

EXAMPLE 28

Preparation of 2-(1-adamantylamino)-4,6-dichloropyrimidine and 4-(1-adamantylamino)-2,6-dichloropyrimidine After adding 40.6 g (225.6 mmoles) of 2,4,6-trichloropyrimidine to a solution of 70.3 g (465.6 mmoles) of 1-aminoadamantane in 650 ml of tetrahydrofuran, the reaction mixture is stirred for 24 hours, then the precipitated crystalline 1-aminoadamantane hydrochloride precipitated is filtered off and the filtrate is evaporated. By subjecting the residue to chromatography on a silica gel column by using a 49:1 mixture of hexane/acetone 2-(1-adamantylamino)-4,6-dichloropyrimidine is obtained which is recrystallized from hexane to result in a yield of 28.74 g (43.5%), m.p.: 151°–155° C.

$^1$H-NMR (60 MHz, CDCl$_3$) δ ppm: 6.55 (s, 1H, 5-H).

By continuing the elution with a 24:1 mixture of hexane/acetone 4-(1-adamantylamino)-2,6-dichloropyrimidine as the more polar product is obtained which is recrystallized similarly from hexane to result in a yield of 35.56 g (53.8%), m.p.: 193°–196° C.

$^1$H-NMR (60 MHz, CDCl$_3$) δ ppm: 6.33 (s, 1H, 5-H).

EXAMPLE 29

Preparation of 2,4-bis(1-adamantylamino)-6-chloropyrimidine

The solution of 26.0 g (87.25 mmoles) of 2-(1-adamantylaminio)-4,6-dichloropyrimidine and 39.5 g (261.6 mmoles) of 1-aminoadamantane in 200 ml of B-butanol is boiled under reflux for 75 hours, then evaporated. The evaporation residue is suspended in 400 ml of ether, filtered off, and the precipitate is dried, then purified by chromatography on a silica gel column, by using chloroform as eluent. The obtained product is recrystallized from ether to obtain the title compound in a yield of 23.94 g (66.44%), m.p.: 232°–236° C.

$^1$H-NMR (60 MHz, CDCl$_3$) δ ppm: 5.64 (s, 1H, 5-H).

EXAMPLE 30

Preparation of 2,4-bis(1-adamantylamino)-6-(1-piperazinyl)pyrimidine

The reaction of 2,4-bis(1-adamantylamino)-6-chloropyrimidine with piperazine as described in Example 4 gives the title compound in a yield of 83.36%, m.p.: 168°–175° C.

$^1$H-NMR (60 MHz, CDCl$_3$) δ ppm: 4.97 (s, 1H, 5-H).

EXAMPLE 31

Preparation of 2-(1-adamantylamino)-4-chloro-6-pyrrolidinopyrimidine

By reacting 2-(1-adamantylamino)-4,6-dichloropyrimidine with pyrrolidine as described in Example 12, the title compound is obtained in a yield of 86%, m.p.: 178°–180° C.

$^1$H-NMR (60 MHz, CDCl$_3$) δ ppm: 5.62 (s, 1H, 5-H).

EXAMPLE 32

Preparation of 2-(1-adamantylamino)-4-(1-piperazinyl)-6-pyrrolidinopyrimidine

By reacting 2-(1-adamantylamino)-4-chloro-6-pyrrolidinopyrimidine with piperazine as described in Example 4, the title compound is obtained in a yield of 69.7%, m.p.: 160°–164° C.

$^1$H-NMR (60 MHz, CDCl$_3$) δ ppm: 4.87 (s, 1H, 5-H).

EXAMPLE 33

Preparation of 4-(1-adamantylamino)-6-chloro-2-pyrrolidinopyrimidine 4-(1-Adamantylamino)-2,6-dichloropyrimidine is reacted with pyrrolidine as described in Example 12 to obtain the title product in a yield of 80.2%, m.p.: 186°–190° C.

$^1$H-NMR (60 MHz, CDCl$_3$) δ ppm: 5.63 (s, 1H, 5-H).

EXAMPLE 34

Preparation of 4-(1-adamantylamino)-6-(1piperazinyl)-2-pyrrolidinopyrimidine 4-(1-Adamantylamino)-6-chloro-2-pyrrolidinopyrimidine is reacted with piperazine as described in Example 4 to give the title compound in a yield of 49.7%, m.p.: 152°–156° C.

$^1$H-NMR (60 MHz, CDCl$_3$) δ ppm: 4.84 (s, 1H, 5-H).

EXAMPLE 35

Preparation of 4,6-dichloro-2-(2,2,6,6-tetramethyl-1-piperidinyl)pyrimidine

The mixture of 25 g (136.3 mmoles) of 2,4,6-trichloropyrimidine and 46.3 ml (272.6 mmoles) of 2,2,6,6-tetramethylpiperidine is boiled under reflux for 50 hours, then cooled down and suspended in 250 ml of hexane. The insoluble material is filtered off, the filtrate is evaporated and the evaporation residue is distributed between 300 ml of chloroform and 50 ml of 10% sodium hydroxide solution. After separation the organic phase is washed 4 times with 100 ml of water each, then dried and evaporated. The evaporation residue is purified by chromatography by using hexane as eluent. After recrystallization of the obtained product from hexane, the title compound is obtained in a yield of 8.04 g (20.47%), m.p.: 89°–90° C.

$^1$H-NMR (60 MHz, CDCl$_3$) δ ppm: 6.53 (s, 1H, 5-H).

EXAMPLE 36

Preparation of 4-chloro-2-(2,2,6,6-tetramethyl-1-piperidinyl)-6-pyrrolidinopyrimidine 4,6-Dichloro-2-(2,2,6,6-tetramethyl-1-piperidinyl)pyrimidine is reacted with pyrrolidine as described in Example 12 to give the title compound in a yield of 75.08%, m.p.: 130°–135° C.

$^1$H-NMR (60 MHz, CDCl$_3$) δ ppm: 5.76 (s, 1H, 5-H).

EXAMPLE 37

Preparation of 2-(2,2,6,6-tetramethyl-1-piperidinyl)-4-(1-piperazinyl)-6-pyrrolidinopyrimidine 4-Chloro-2-(2,2,6,6-tetramethyl-1-piperidinyl)-6-pyrrolidinopyrimidine is reacted with piperazine as described in Example 42 to give the title compound in a yield of 80.2%, m.p.: 134°–137° C.

$^1$H-NMa (60 MHz, CDCl$_3$) δ ppm: 5.01 (s, 1H, 5-H).

EXAMPLE 38

Preparation of 2-(4,4-ethylenedioxy-1-piperidinyl)-4,6-dichloropyrimidine and 4-(4,4-ethylenedioxy-1-piperidinyl)-2,6-dichloropyrimidine After dropwise adding 43.32 g (286 mmoles) of 1,4-dioxa-8-azaspiro[4,5]decane to a solution of 25 g (136.3 mmoles) of 2,4,6-trichloropyrimidine in 200 ml of tetrahydrofuran at 0° C., the reaction mixture is stirred at room temperature for 1 hour, then evaporated. The residue is distributed between 300 ml of chloroform and 100 ml of 10% sodium hydroxide solution. After separating the organic phase is washed 4 times with 100 ml of water each, then dried and evaporated. The evaporation residue is subjected to chromatography on a silica gel column by using chloroform as eluent. The less polar 2-(4,4-ethylenedioxy-1-piperidinyl)-4,6-dichloropyrimidine is recrystallized from ethyl acetate to result in a yield of 13.98 g (35.36%), m.p.: 104°–105° C.

$^1$H-NMR (60 MHz, CDCl$_3$) δ ppm: 6.50 (s, 1H, 5-H).

The more polar 4-(4,4-ethylenedioxy-1-piperidinyl)-2,6-dichloropyrimidine is also recrystallized from ethyl acetate to result in a yield of 20.98 g (53.04%), m.p.: 133°–136° C.
$^1$H-NMR (60 MHz, CDCl$_3$) δ ppm: 6.40 (s, 1H, 5-H).

EXAMPLE 39

Preparation of 2,4-bis(4,4-ethylenedioxy-1-piperidinyl)-6-chloropyrimidine

After adding 2.6 ml (17.23 mmoles) of 1,4-dioxa-8-azaspiro[4,5]decane to the solution of 2.0 g (6.89 mmoles) of 2-(4,4-ethylenedioxy-1-piperidinyl)-4,6-dichloropyrimidine in 40 ml of n-butanol, the reaction mixture is boiled under reflux for 4 hours, then evaporated. The evaporation residue is distributed between 50 ml of chloroform and 5 ml of 10% sodium hydroxide solution. After separation the organic phase is washed 4 times with 10 ml of water each, then dried and evaporated. After recrystallizing the obtained product from hexane the title compound is obtained in a yield of 2.51 g (91%), m.p.: 130°–131° C.
$^1$H-NMR (60 MHz, CDCl$_3$) δ ppm: 5.88 (s, 1H, 5-H).

Example 40

Preparation of 2,4-bis(4,4-ethylenedioxy-1-piperidinyl)-6-(1-piperazinyl)pyrimidine The reaction of 2,4-bis(4,4-ethylenedioxy-1-piperidinyl)-6-chloropyrimidine with piperazine as described in Example 4 gives the title compound in a yield of 55.7%, m.p.: 130°–140° C.
$^1$H-NMR (60 MHz, CDCl$_3$) δ ppm: 5.01 (s, 1H, 5-H).

Example 41

Preparation of 2,4-bis(4,4-ethylenedioxy-1-piperidinyl)-6-chloropyrlmidine and 4,6-bis(4,4-ethylenedioxy-1-piperidinyl)-2-chloropyrimidine After adding 26 ml (172.3 mmoles) of 1,4-dioxa-8-azaspiro[4,5]decane to a solution of 20.0 g (68.9) mmoles) of 2-(4,4-ethylenedioxy-1-piperidinyl)-4,6-dichloropyrimidine in 400 ml of n-butanol, the reaction mixture is boiled under reflux for 4 hours, then evaporated. The evaporation residue is distributed between 500 ml of chloroform and 50 ml of 10% sodium hydroxide solution. After separation the organic phase is washed 4 times with 100 ml of water each, then dried and evaporated. The evaporation residue is subjected to chromatography by using chloroform as eluent on a silica gel column. The less polar 2,4-bis(4,4-ethylenedioxy-1-piperidinyl)-6-chloropyrimidine is recrystallized from ethyl acetate to give a yield of 16.58 g (73.6%), m.p.: 130°–131° C.
$^1$H-NMR (60 MHz, CDCl$_3$) δ ppm: 5.87 (s, 1H, 5-H).

The more polar 4,6-bis(4,4-ethylenedioxy-1-piperidinyl)-2--chloropyrimidine is also recrystallized from ethyl acetate to result in a yield of 2.66 g (11.8%), m.p.: 149°–150° C.
$^1$H-NMR (60 MHz, CDCl$_3$) δ ppm: 5.48 (s, 1H, 5-H).

EXAMPLE 42

Preparation of 4,6-bis(4,4-ethylenedioxy-1-piperidinyl)-2-(1-piperazinyl)pyrimidine The reaction of 4,6-bis(4,4-ethylenedioxy-1-piperidinyl)-2-chloropyrimidine with piperazine as described in Example 4 gives the title compound in a yield of 58.9%, m.p.: 122°–126° C.
$^1$H-NMR (60 MHz, CDCl$_3$) δ ppm: 4.99 (s, 1H, 5-H).

EXAMPLE 43

Preparation of 2-cyclopentylamino-4,6-dichloroplrrimidine and 2,6-dichloro-4-cyclopentylaminopyrimidine 2,4,6-Trichloropyrimidine is reacted with cyclopentylamine as described in Example 2 to obtain the less polar 2-cyclopentylamino-4,6-dichloropyrimidine in a yield of 35.2%, m.p.: 48°–52° C.
$^1$H-NMR (60 MHz, CDCl$_3$) δ ppm: 6.52 (s, 1H, 5-H).

The more polar 2,6-dichloro-4-cyclopentylaminopyrimidine is obtained as an oily product in a yield of 57.2%.
$^1$H-NMR (60 MHz, CDCl$_3$) δ ppm: 6.30 (s, 1H, 5-H).

EXAMPLE 44

Preparation of 2-cyclopentylamino-4-chloro-6-pyrrolidinopyrimidine

2-Cyclopentylamino-4,6-dichloropyrimidine is reacted with pyrrolidine as described in Example 12 to give the title compound as an oily product in a yield of 72.4%.
$^1$H-NMR (60 MHz, CDCl$_3$) δ ppm: 5.72 (s, 1H, 5-H).

EXAMPLE 45

Preparation of 2-cyclopentylamino-4-(1-piperazinyl)6-pyrrolidinopyrimidine 2-Cyclopentylamino-4-chloro-6-pyrrolidinopyrimidine is reacted with piperazine as described in Example 4 to afford the title compound in a yield of 63.8%, m.p.: 125°–128° C.
$^1$H-NMR (60 MHz, CDCl$_3$) δ ppm: 4.84 (s, 1H, 5-H).

EXAMPLE 46

Preparation of 6-chloro-2,4-bis(2,2-dimethylpropylamino)pyrimidine and 2-chloro-4,6-bis(2,2-dimethylpropylamino) pyrimidine After dropwise adding 5.00 g (27.26 moles) of 2,4,6-trichloropyrimidine to the solution of 11.88 g (136.3 mmoles) of 1-amino-2,2-dimethylpropane in 50 ml of isopropanol while cooling and stirring, the reaction mixture is boiled under reflux for 20 hours, then evaporated. The evaporation residue is distributed between 80 ml of chloroform and 25 ml of 10% sodium hydroxide solution. After separation the organic phase is washed 4 times with 20 ml of water each, then dried and evaporated. The evaporation residue is subjected to chromatography by using a mixture of hexane and ethyl acetate as eluent on a silica gel column. By carrying out the elution with a 99:1 mixture, 6-chloro-2,4-bis(2,2-dimethylpropylamino)pyrimidine is obtained which is recrystallized from hexane to give a yield of 5.74 g (73.9%), m.p.: 95°–97° C.

By continuing the elution with a 19:1 mixture of hexane/ethyl acetate, the more polar 2-chloro-4,6-bis(2,2-dimethylpropylamino)pyrimidine is obtained which is recrystallized from hexane to give a yield of 0.16 g (2.8%), m.p.: 178°–185° C.

EXAMPLE 47

Preparation of 21-(4-bromobenzenesulfonyloxy)-16α-methylpregna-1,4,9(11)-triene-3,20-dione To a solution containing 10.0 g (29.4 moles) of 21-hydroxy-16α-methylpregna-1,4,9(11)-triene-3,20-dione in 100 mol of tetrahydrofuran, first 7,14 ml (51.4 mmoles) of triethylamine, then at 0° C. 13.1 g (51.4 moles) of 4-bromobenzenesulfonyl chloride are added, the reaction mixture is stirred at room temperature for 4 hours, then it is dropwise added to 450 ml of water while stirring. The precipitate is filtered off, dried and recrystallized from ether to obtain 11.0 g (67.07%) of the title compound, m.p.: 124°–129° C.

$^1$H-NMR (300 MHz, CDCl$_3$) δ ppm: 0.65 (s, 3H, 18-CH$_3$), 0.93 (d, 1H, 16α-CH$_3$), 1.40 (s, 3H, 19-CH$_3$), 4.54 és 4.66 (d, d, 2H, 21-CH$_2$), 5.50 (m, 1H, 11-H), 6.07 (t, 1H, 4-H), 6.29 (dd, 1H, 2-H), 7.16 (d, 1H, 16H), 7.72 (d, 2H, phenylene C3-H), C5-H), 7.83 (d, 2H, phenylene C2-H, C6-H).

EXAMPLE 48

Preparation of 21-{4-[2,4-bis(1-adamantylamino)-6-pyrimidinyl]-1-piperazinyl}-16α-methylpregna-1,4,9(11)-triene-3,20-dione.

After adding 1.88 g (4.07 moles) of 2,4-bis(1-adamantylamino)-6-(1-piperazinyl)pyrimidine and 0.56 g of potassium carbonate to a solution containing 2.00 g (3.57 mmoles) of 21-(4-bromobenzenesulfonyloxy)-16α-methylpregna-1,4,9(11)-triene-3,20-dione in 100 ml of acetonitrile, the reaction mixture is stirred at 65° C. for 5 hours, then evaporated. The residue is distributed between 40 ml of chloroform and 10 ml of water. After separation the chloroform solution is dried, evaporated and the residue is purified by chromatography on a silica gel column. A 98:2 mixture of chloroform/methanol is used for elution and the product obtained is recrystallized from ether to give the title compound in a yield of 2.48 g (88.5%), m.p.: 210°–220° C.

$^1$H-NMR (250 MHz, CDCl$_3$) δ ppm: 0.68 (s, 3H, 18-CH$_3$), 0.96 (d, 1H, 16α-CH$_3$), 1.40 (s, 3H, 19-CH$_3$), 3.13 and 3.23 (d, d, 2H, 21-CH$_2$), 4.98 (s, 1H, pyrimidine, C5-H), 5.51 (m, 1H, 11-H), 6.07 (m, 1H, 4-H), 6.28 (d, d, 1H, 2-H), 7.16 (d, 1H, 1-H).

EXAMPLE 49

Preparation of 2,4-bis(1-adamantylamino)-6-chloropyrimidine and 4,6-bis(1-adamantylamino)-2-chloropyrimidine 26.0 g (87.25 mmoles) of 4-(1-adamantylamino)-2,6-dichloropyrimidine and 39.5 g (261.6 mmoles) of 1-aminoadamantane are dissolved in 200 ml of n-butanol, then the reaction mixture is boiled for 75 hours and evaporated. The residue is suspended in 400 ml of ether and filtered. The recovered material is chromatographed after drying on a silica gel column by using chloroform as eluent. The obtained substance is a mixture of the title isomers. These are separated on a silica gel column by using a mixture of hexane and ethyl acetate. By using a 49:1 mixture of these solvents as eluent 2,4-bis(1-adamantylamino)-6-chloropyrimidine is obtained which is recrystallized to obtain a yield of 21.67 g (60.14%).

By continuing the elution with a 6:1 mixture of said solvents the more polar 4,6-bis(1-adamantylamino)-2-chloropyrimidine is obtained which is recrystallized from hexane to obtain a yield of 1.88 g (5.22%), melting point: 260°–266° C.

$^1$H-NMR (250 MHz, CDCl$_3$) δ ppm: 5.49 (s, 1H, 5-H).

EXAMPLE 50

Preparation of 4,6-bis(1-adamantylamine)-2-(1-piperazinyl)-pyrimidine 4,6-Bis(1-adamantylamino)-2-chloropyrimidine is reacted with piperazine as described in Example 4 to obtain the title compound in a yield of 94.4%, m.p.: 210°–220° C.

$^1$H-NMR (60 MHz, CDCl$_3$) δ ppm: 4.97 (s, 1H, 5-H).

EXAMPLE 51

Preparation of 2,4-bis(cyclopentylamino)-6-chloropyrimidine 5.0 g of 2-(cyclopentylamino)-4,6-dichloropyrimidine are dissolved in 25 ml of isopropanol, then 7.5 ml of cyclopentylamine are added and the mixture is boiled for 6 hours. Then the reaction mixture is evaporated, the residue is separated between 80 ml of chloroform and 15 ml of 10% sodium hydroxide solution. After separation the organic phase is washed 4 times with 20 ml of water each, dried and evaporated. The title compound is obtained by recrystallizing from hexane in a yield of 5.24 g (86.7%), m.p.: 94°–98° C.

$^1$H-NMR (60 MHz, CDCl$_3$) δ ppm: 5.67 (s, 1H, 5-H).

EXAMPLE 52

Preparation of 2,4-bis(cyclopentylamino)-6-(1-piperazinyl)pyrimidine 2,4-Bis(cyclopentylamino)-6-chloropyrimidine is reacted with piperazine as described in Example 4 to give the title compound in a yield of 81.9%, m.p.: 142°–148° C.

$^1$H-NMR (60 MHz, CDCl$_3$) δ ppm: 4.94 (s, 1H, 5-H).

We claim:

1. A compound selected from the group consisting of: 2,4-bis[1-adamantylamino]-6-(1-piperazinyl)pyrimidine; and 4,6-bis(1-adamantylamino)-2 -(1-piperazinyl)pyrimidine; or a pharmaceutically acceptable acid addition salt thereof.

2. 2,4-bis[1-adamantylamino]-6-(1-piperazinyl)pyrimidine or a pharmaceutically acceptable acid addition salt thereof as defined in claim 1.

\* \* \* \* \*